(12) United States Patent
Müller

(10) Patent No.: US 9,538,966 B2
(45) Date of Patent: Jan. 10, 2017

(54) COMPUTED TOMOGRAPHY APPARATUS FOR ODONTOLOGY

(75) Inventor: Timo Müller, Espoo (FI)

(73) Assignee: PLANMECA OY, Helsinki (FI)

( * ) Notice: Subject to any disclaimer, the term of this patent is extended or adjusted under 35 U.S.C. 154(b) by 284 days.

(21) Appl. No.: 13/512,148

(22) PCT Filed: Nov. 23, 2010

(86) PCT No.: PCT/FI2010/050950
§ 371 (c)(1),
(2), (4) Date: Aug. 30, 2012

(87) PCT Pub. No.: WO2011/070227
PCT Pub. Date: Jun. 16, 2011

(65) Prior Publication Data
US 2012/0314835 A1    Dec. 13, 2012

(30) Foreign Application Priority Data
Nov. 25, 2009    (FI) ..................... 20090443

(51) Int. Cl.
*A61B 6/14* (2006.01)
*A61B 6/03* (2006.01)
*A61B 6/00* (2006.01)

(52) U.S. Cl.
CPC ............... *A61B 6/14* (2013.01); *A61B 6/032* (2013.01); *A61B 6/40* (2013.01); *A61B 6/405* (2013.01);
(Continued)

(58) Field of Classification Search
CPC ........... A61B 6/025; A61B 6/027; A61B 6/03; A61B 6/032; A61B 6/14; A61B 6/4429; A61B 6/4435; A61B 6/4441; A61B 6/501; A61B 6/54; A61B 6/40; A61B 6/5229; A61B 6/5241
(Continued)

(56) References Cited

U.S. PATENT DOCUMENTS 6,069,938 A * 5/2000 Chornenky .......... A61N 5/1001
378/122
6,118,842 A * 9/2000 Arai ....................... A61B 6/032
378/38
(Continued)

FOREIGN PATENT DOCUMENTS

FI    WO 2006097576 A1 *  9/2006  ............... A61B 6/14
WO   WO 2006097576        9/2006
WO   WO 2006097576 A1 *  9/2006  ............... A61B 6/14

OTHER PUBLICATIONS

Hsieh, J., "Computed Tomography: Principles, Design, Artifacts and Recent Advantages".

*Primary Examiner* — David E Smith
(74) *Attorney, Agent, or Firm* — Fay Sharpe LLP

(57) ABSTRACT

Computed tomography apparatus for odontology, which includes an arm part arranged to be turnable, to which arm part at a distance from each other a radiation source and a receiver of image information have been arranged, in which apparatus said arm part is arranged to locate or to be transferred to such location with respect to the volume desired to be imaged that when the arm part is turned during the imaging, at least over a substantial angular range only a portion of the volume arranged to become imaged is within the radiation beam, and in which the control system of the apparatus comprises a control routine which then controls said radiation source to generate radiation as pulsed.

14 Claims, 3 Drawing Sheets

(52) U.S. Cl.
CPC ........... *A61B 6/5229* (2013.01); *A61B 6/5241* (2013.01); *A61B 6/4085* (2013.01); *A61B 6/4441* (2013.01); *A61B 6/482* (2013.01)

(58) Field of Classification Search
USPC .................................. 378/4, 16, 19, 38–40
See application file for complete search history.

(56) References Cited

U.S. PATENT DOCUMENTS

| | | | | |
|---|---|---|---|---|
| 6,233,305 | B1* | 5/2001 | Muller | G01N 23/046 378/10 |
| 6,385,280 | B1 | 5/2002 | Bittl | |
| 7,486,759 | B2* | 2/2009 | Suzuki | A61B 6/14 378/38 |
| 2004/0068169 | A1 | 4/2004 | Mansfield et al. | |
| 2005/0058251 | A1* | 3/2005 | Spahn | H05G 1/30 378/114 |
| 2005/0117693 | A1* | 6/2005 | Miyano | A61B 6/0478 378/4 |
| 2006/0109951 | A1 | 5/2006 | Popescu | |
| 2007/0051976 | A1* | 3/2007 | Moody | H01L 27/14609 257/186 |
| 2007/0269001 | A1* | 11/2007 | Maschke | A61B 6/14 378/38 |
| 2008/0137802 | A1 | 6/2008 | Suzuki | |
| 2008/0260092 | A1 | 10/2008 | Imai et al. | |
| 2009/0232275 | A1 | 9/2009 | Spartiotis et al. | |
| 2012/0321035 | A1* | 12/2012 | Muller | A61B 6/14 378/4 |

\* cited by examiner

COMPUTED TOMOGRAPHY APPARATUS FOR ODONTOLOGY

FIELD OF INVENTION

This invention relates to a computed tomography apparatus designed for dental use, especially to a so-called offset imaging and to a related arrangement for controlling a radiation source of the imaging apparatus during an imaging process.

BACKGROUND OF INVENTION

Medical X-ray imaging has a long history. The earliest techniques were based on transilluminating the object being imaged. In transillumination, all the anatomies of the volume being imaged possibly overlapping in the direction of radiation are imaged on film on top of each other. Concerning layer imaging, i.e. a so-called tomographic imaging, on the other hand, one may get in the image being formed a desired layer of the object to become imaged more clearly by causing blurring of the other layers of the object. Depending on the imaging procedure, blurring is accomplished by changing the relative position of the imaging means and the object in a controlled manner during the imaging event either during irradiation or between individual irradiations. Especially along with advancement of computers and digital imaging, a great number of different tomographic imaging techniques and devices have been developed.

In the field of odontology, in addition to intra-oral and cephalometric imaging which are simpler as far as imaging technology is concerned as they are realized by transillumination imaging one generally uses, among other things, a so-called panoramic imaging in which, typically, a layer comprising the whole dental arch is imaged on a plane. In conventional film-based panoramic imaging, one scans over the dental arch with a narrow beam such that the centre of rotation of a turnable arm part, substantially to the opposite ends of which the imaging means have been positioned, is transferred linearly while the arm part is turned and the film moving together with the arm part is transferred through the narrow beam produced by a radiation source with a speed fulfilling the imaging condition of the imaging procedure in question. In digital panoramic imaging, the frequency at which image data is read from the sensor during an imaging scan corresponds this transfer speed of the film.

One has also begun to apply computer (or computed) tomography (CT), used earlier predominantly in hospital environment, in the field of odontology. As such, one is not able to transfer these massive and expensive CT apparatuses used in hospitals to a typical dental clinic environment, already on account of the size of the apparatuses but especially on account of their price.

Imaging-technically, several different CT technologies are known today. In CT imaging, the volume to be imaged is irradiated from different directions and, from the data thus acquired, a desired two- or three-dimensional image is reconstructed afterwards. In principle, using this kind of technology one is also able to reconstruct, among other things, a two-dimensional image outspread on a plane of a part of the dental arch or, if desired, of the whole dental arch. As far as principles of computed tomography and its different applications are concerned, a reference can be made to the literature on the art, such as to *Computed Tomography: Principles, Design, Artifacts and Recent Advantages*, Jian Hsieh, SPIE PRESS, 2003, Bellingham, Wash., USA.

One form of computed tomography is the so-called cone beam CT (CBCT) in which one uses, as a distinction from the narrow beam used e.g. in panoramic imaging and conventional CT imaging, a beam substantially the size of the dimensions of the volume to be imaged and, respectively, instead of a slot sensor, a detector the size of which corresponds the size of the beam in question. Compared to several more conventional CT imaging technologies, the CBCT technology is able to provide significantly smaller radiation doses and shorter imaging times.

A typical starting point in some of the CT solutions outlined and realized for odontology has been arranging the imaging means to a relatively massive, stable support construction in which the patient is positioned in a sitting position on a chair in between the imaging means, and the possible relative motions of the patient location and the imaging means, for positioning the imaging means ready for imaging a desired volume, are realized by moving the chair. On the other hand, e.g. U.S. Pat. No. 6,118,842 outlines a structure based on a traditional dental panoramic apparatus by which one is able to both turn the imaging means with respect to the centre of rotation and to change the position of the centre of rotation by means of a moving mechanism of the arm part comprising the imaging means. The dimensions of this apparatus and those of the detector used in it enable gathering information for reconstructing a volume of a certain portion of the skull but, in case of desiring to acquire larger, several or e.g. adjacent volumes reconstructed by the apparatus, one has to repeat the imaging by first arranging the relative position of the object and the imaging means according to the new target area to be imaged.

The size of the volume being imageable by one rotation of the imaging means can be increased with the so-called offset imaging. One known manner to realize such imaging is to arrange the imaging sensor movable before imaging to such a position with respect to the target area in which, when rotating the imaging means, at each moment of time only part of the area desired to be imaged is in the beam but, when the whole rotation has been completed, all of the partial areas of the target area have been covered at an angle range of essentially at least 180 degrees. A corresponding result is also reached by moving the position of the centre of rotation of the imaging means, such as in connection with an apparatus described in U.S. Pat. No. 7,486,759, which specification is attached hereto to also more comprehensively depicting the principles of offset imaging according to prior art.

In the above-mentioned U.S. Pat. No. 7,486,759, one essential idea of the solution is to realize an imaging scan of 360 degrees with one exposure of extended duration. This kind of exposure loads the radiation source, which may prove to be problematic especially in such combination x-ray apparatus being originally designed for use that loads the source of radiation less.

An object of the present invention and its preferable embodiments is to provide novel solutions for imaging a greater volume by one imaging than what is possible when the imaging is realized in a conventional manner by using an arm part, in which are arranged at a distance from each other a source of radiation and a receiver of image information, and when both the centre of rotation of the arm part in question and the central axis of the beam are arranged to travel and remain for the whole duration of the imaging process in the middle of the area desired to be imaged.

BRIEF DESCRIPTION OF INVENTION

The essential features of the invention are presented in the accompanying patent claims. It is essential for the dental CT apparatus according to the invention that it comprises a control system which enables an offset imaging process which loads the source of radiation less than e.g. the arrangement described in the U.S. Pat. No. 7,486,759. According to the invention, this can be reached by pulsing the radiation and preferably the pulsing is realized as so controlled that the anode current of the radiation source is measured and based on this measurement, duration of the pulses is adjusted in case needed so that the radiation dose each of the pulses produces is always essentially the same.

BRIEF DESCRIPTION OF DRAWINGS

Next, the invention, its preferable embodiments and their objectives and advantages will be described in more detail also with reference to the enclosed figures, of which

DETAILED DESCRIPTION OF INVENTION

Figure 1A:
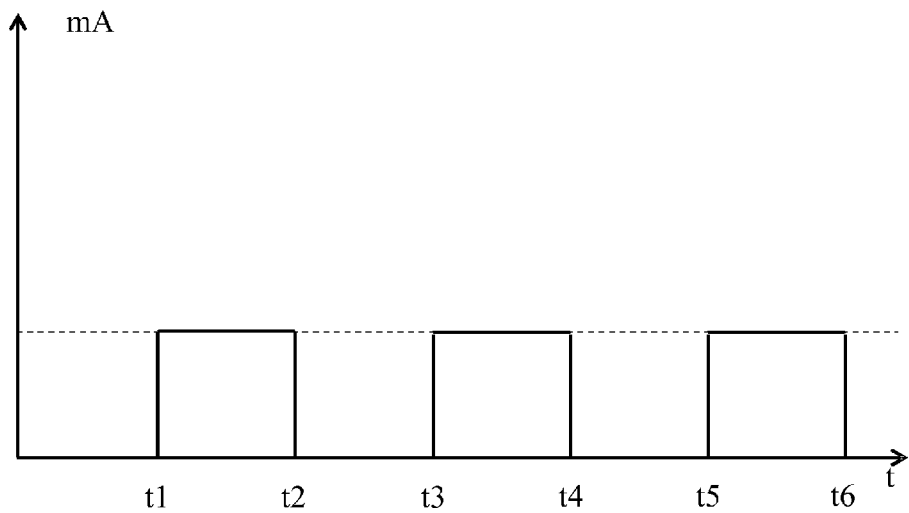
FIGS. 1a and 1b show pulsing of radiation according to the invention during asymmetrical imaging.

Thus, it is essential to the invention that the so-called offset imaging, known as such in connection with CT imaging, is carried out by pulsed radiation. Offset imaging can be defined to be an imaging mode wherein, while the imaging means are rotated during the imaging, only a part of the volume arranged to become imaged is in the beam over a substantial or the whole angular range used in the imaging. Rotation of 360 degrees about the region desired to become imaged is needed in a typical offset imaging, whereas in a symmetrical case, enough information for the back projection will be acquired even by movement of 180 degrees. The wider angle of rotation leads to a longer imaging time and thus, among others, to increase of the load for the radiation source. FIG. 1a shows pulsed anode current of a radiation source as a function of time according to an ideal situation, when the radiation source generates pulses of constant magnitude and duration, at a regular frequency.

Figure 1B:
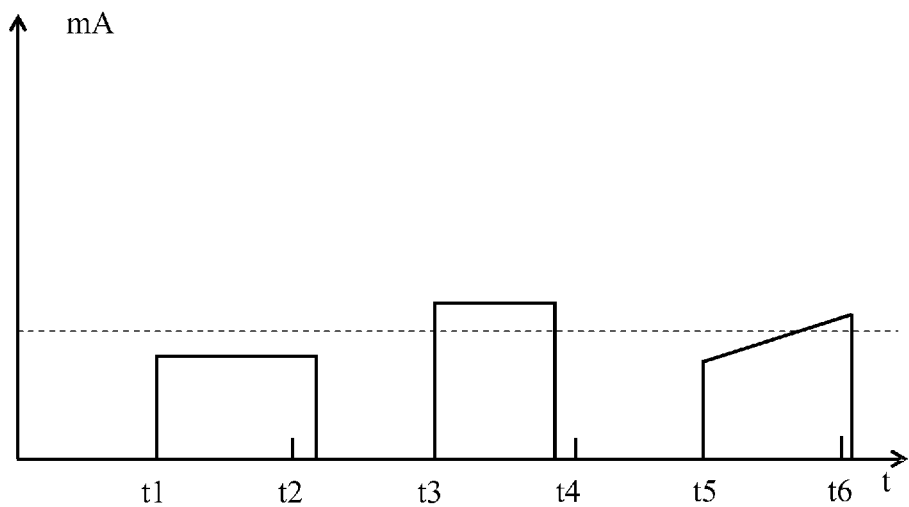

FIG. 1b, on the other hand, shows a preferable embodiment of the invention in which pulses are still generated at a constant frequency but in which the deviations from the set values detected in the anode current measurement are compensated by adjusting duration of the pulse longer or shorter such that the integral, as shown by the areas in FIG. 1b, remains constant.

The last pulse of FIG. 1b illustrates that the anode current is not necessary constant even during individual pulses but, according to this embodiment of the invention, also a change occurring during a pulse can be compensated by cutting off the tube voltage in accordance with how the anode current varies during each pulse.

More generally speaking, according to a preferable embodiment of the invention, instead of a customarily used constant periodic pulsing, the pulsing of the source of radiation is adjusted such that the starting frequency of pulses is kept constant but the duration of each pulse is determined based on the respective anode current at a time. This arrangement is based on compensating the technical problem of the spectrum produced by the source of radiation not typically remaining totally constant as a function of time.

Thus, the invention includes measuring the anode current of the source of radiation and, differently from arrangements according to prior art in which e.g. the acceleration voltage of the source of radiation is adjusted based on such a measurement, here duration of the pulses is controlled. The control is done such that the radiation dose produced by each pulse (mA×s) is kept constant, i.e., the pulse is terminated at the instant the integral of the current reaches a preset level. Such control is quicker than e.g. the aforementioned voltage control and, regarding the imaging, it is more relevant to keep the actual dose constant than the voltage, which affects the dose indirectly. Such accurate adjustment of the radiation source is advantageous particularly in the offset imaging according to the invention in which the imaging process is quite long as the imaging means turns for the full 360 degrees, which requires time and thus, the load for the radiation source becomes great.

The control system of the apparatus used in the invention is provided with control routines to enable, on the one hand, pulsed operation of the source of radiation 14 and, on the other hand, saving the information detected by the imaging detector 15 and/or forwarding it periodically. Preferably, the information of the sensor is arranged readable several times a second, such as e.g. more than 10 times a second. It is preferable to synchronize the periodization of irradiation with the operation of the sensor such that the irradiation is always interrupted when information is read out from the sensor. The frequency rate is preferably arranged at least such that duration of the radiation pulse corresponds that maximum distance the beam travels in the volume being imaged which corresponds the voxel size one intends to use in the reconstruction—or said differently, duration of the radiation pulse is arranged shorter than the maximum time it can take for the beam to turn in the volume being imaged for a distance which corresponds the voxel size one intends to use in the reconstruction. Duration of the radiation pulses can also be arranged shorter, even substantially shorter than the time it takes for the imaging sensor to move during imaging for a distance of one sensor pixel. The pixel size of the imaging sensor can be arranged to be of the order of 200 μm, but even smaller as technology advances. The imaging sensor is arranged in functional connection with a computer, which computer comprises means for reconstructing a two- and/or three-dimensional image of the information detected by the sensor.

Pulsing of radiation also offers a preferable way to realize a so-called double energy imaging in connection with offset imaging. Double energy imaging has been used in connection with determining bone properties. According to the invention, double energy imaging may be realised by e.g. alternately using in the imaging, while rotation of the imaging means advances, pulses generated by a first and a second voltage, but other ways to alter the voltage may obviously be used as well. One such way is to generate pulses as consecutive sequences, in which always the same number of pulses is generated first by the other, then by the other voltage.

FIGS. 2a-2c show one preferable arrangement for realizing offset imaging according to the invention. The Figs. show a CT apparatus, which includes a first arm part 11 comprising imaging means (a radiation source 14 and a receiver of image information 15) and a second arm part 12 supporting the said arm part 11. The first arm part 11 is arranged turnable with respect to the second arm part 12 about a first rotation axis 21 which connects said arm parts 11, 12. The radiation source 14 and the receiver of image information 15 are arranged on the first arm part 11 at a distance from each other on opposite sides of the rotation axis 21. The apparatus includes a control system not shown in the attached Figs. and at least one actuator 31, 32 (see FIG. 4), which is arranged to drive at least the first arm part 11 and/or the second arm part 12 about their rotation axis 21. The arm part 12 supporting the arm part 11 which supports the imaging means 14, 15 is further supported via a support arm 13 to a support structure 10. (For the sake of clarity and generality, the object to be imaged is drawn in this context as "a bone", instead of a skull or teeth which it would be in reality, when considering the invention at hand.)

FIGS. 2a-2c show an arm structure according to a preferable embodiment of the invention arranged to realize an imaging mode according to the invention. In this arrangement, the first arm part 11 supporting the imaging means 14, 15 is driven at a desired angle with respect to the second arm part 12 and for the duration of imaging, it is kept stationary with respect to the second arm part 12, while the actual movement of the imaging means 14, 15 during imaging is realized by driving the second arm part 12 about its rotation axis 22. In this arrangement, according to the principle of the offset imaging, the radiation beam does not at all times cover the whole area one wishes to get imaged, nor does the central axis of the radiation beam generated by the radiation source 14 continuously go through the centre of the area one wishes to get imaged but asymmetrically with respect to the area being imaged, an outcome of which being that the arm construction must be rotated for the full 360 degrees in order to cover the whole volume one wishes to be imaged. As a consequence of this asymmetric imaging geometry, though, information for back projection, after the rotation over 360 degrees, has been gathered from a wider area than would be in the case of symmetric imaging.

In the arrangement according to FIGS. 2a-2c, the arm part 12 supporting the arm part 11 supporting the imaging means 14, 15 is arranged to its supporting arm 13 via a second rotation axis 22. This arrangement also enables such imaging modes not shown in the figures, like panoramic imaging, in which the centre of rotation 21 of the arm part 11 supporting the imaging means is moved during imaging. Furthermore, when the supporting arm 13 is also arranged turnable with respect to its own rotation axis 23, the arm part 11 supporting the imaging means 14, 15 can be positioned freely within the operating range of the set of arms 11, 12, 13, which provides versatile alternatives for realizing various imaging geometries.

Figure 2:
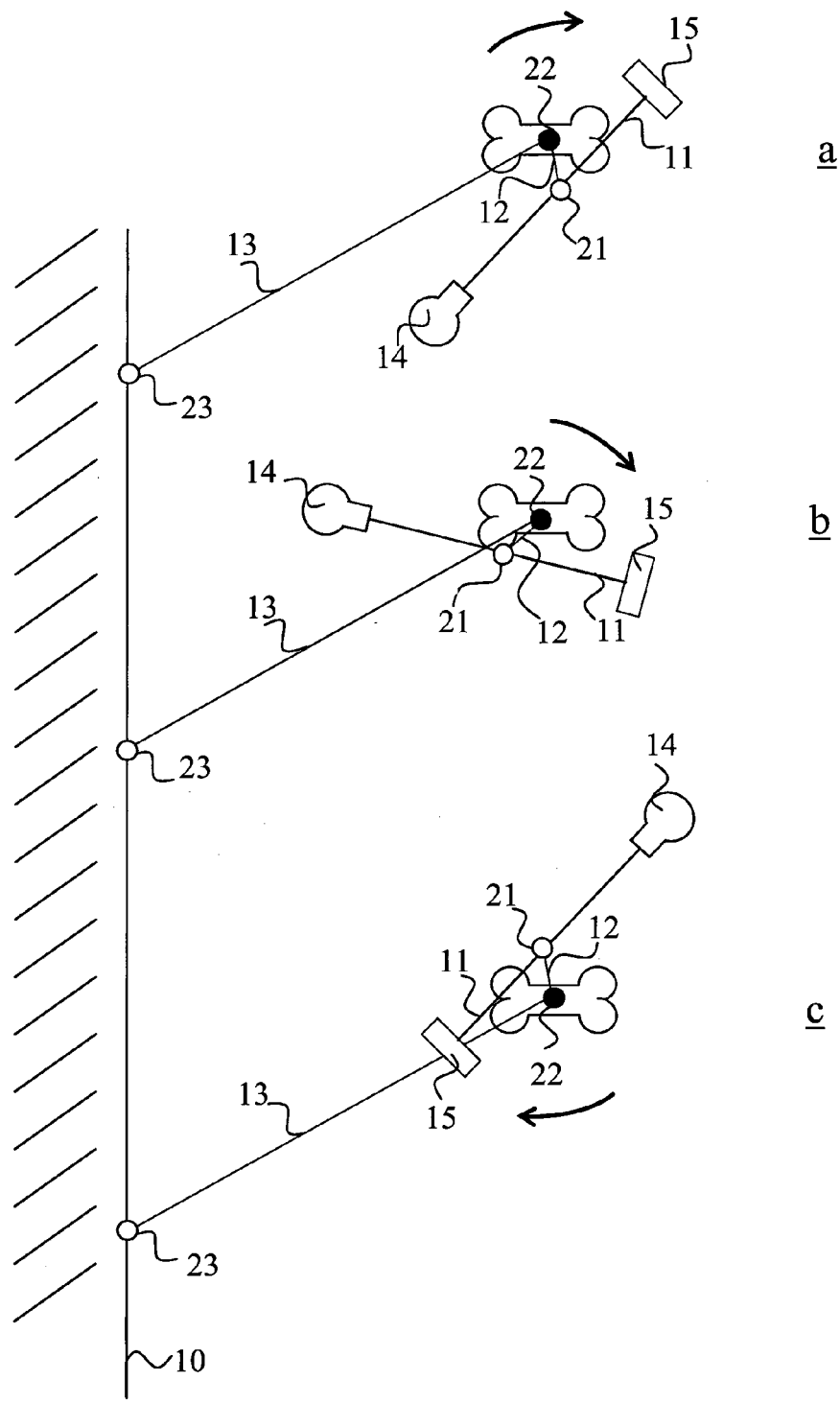
FIGS. 2a-2c show an imaging mode in which a motion during imaging is realized by means of a rotating motion of an arm part supporting an arm part supporting imaging means.

The size of the volume one is able to image using the imaging mode according to FIGS. 2a-2c depends on the angle between the first 11 and the second arm part 12 at which they have been arranged as non-rotatable in relation to each other for the duration of imaging. One preferable embodiment of the invention, which also is not shown individually in the figures, comprises two motions done in opposite rotation directions, the first of which is done e.g. in accordance with FIG. 2 with a constant angle "alpha" between the first 11 and the second arm part 12, but now using turning angle of only 180 degrees, and the return motion of an equivalent turning angle is made otherwise similarly but now with angle "-alpha" between the arm parts in question. When operating in this manner, the rotation mechanism of the set of arms is simpler to realize as one does not have to consider the technical problems entailed by 360 degree rotation. More generally, in this imaging mode the rotation angle of the first motion and its counter-motion does not have to be particularly 180 degrees, but one is able to reach the same end-result by varying this rotation angle and, on the other hand, said angle "alpha" in a corresponding manner. The same Principle is naturally also realizable with arm structures different from the one shown in FIGS. 2a-2c.

Figure 3:
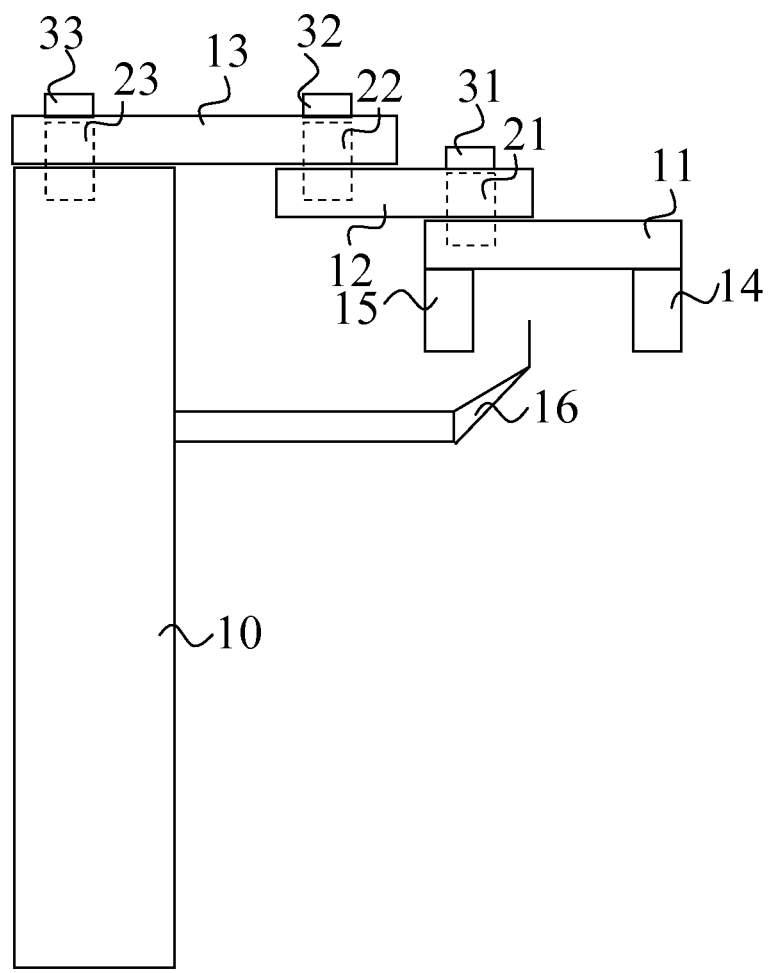
FIG. 3 shows a simplified side view of one solution for a computed tomography apparatus applicable for use in the invention.

The apparatus according to the invention can be realized as shown as simplified in FIG. 3. The support structure 10 is realized in FIG. 3 as a vertical body part 10 which supports the supporting arm 13 and the first 11 and the second arm part 12 connected to it. The first arm part 11 supporting the imaging means 14, 15 is arranged turnable about the rotation axis 21 supported on the second arm part 12 and the second arm part 12 again turnable about the rotation axis 22 supported on the supporting arm 13. In FIG. 3, into connection with the rotation axes 21, 22 are arranged the first and the second actuator 31, 32 which can drive the first 11 and the second arm part 12 as controlled by the control system of the apparatus. According to the invention, the control system comprises control routines for realizing imagings in accordance with FIGS. 2a-2c. In principle, driving the first 11 and the second arm part 12 can also be realized with suitable arrangements by only one actuator. The supporting arm 13 can also be arranged turnable with respect to the support structure 10, in the arrangement according to FIG. 3, as driven by a third actuator 33. It is possible to arrange to the housing part 10 a vertical motion not shown in FIG. 3. The apparatus typically further includes a patient support means 16, which in the arrangement according to FIG. 3 is arranged in the body part 10. The supporting arm 13 can also be attached e.g. to a ceiling or wall, whereby the patient support means 16 may be arranged in some other fixed location with respect to the set of arms 11, 12, 13 of the apparatus.

In the apparatus having a vertical body part 10 according to FIG. 3, the vertical motion can be realized e.g. such that the patient support means 16 is made to move along the vertical motion of the arm construction 11, 12, 13 or such that the patient support means 16 and the arm construction 11, 12, 13 are provided with vertical freedom of movement independent of each other. With such a construction, the position of the volume being imaged may be arranged at a desired point within the operating range of the set of arms 11, 12, 13 both in horizontal and vertical direction, without moving the patient.

The imaging apparatus according to the invention can be arranged into connection with a separate computer such that the CT apparatus itself does not necessarily have to comprise means for processing the information detected by the detector 15. The detector 15 used in the apparatus can be e.g. a CMOS sensor or one based on so-called direct detection. It is possible to reconstruct an image of the information detected by the sensor with methods known as such, such as the so-called filtered or iterative back projection algorithms.

In the apparatus according to the invention, the desired coordinates of the rotation axes 21, 22 and orientations of the arm parts 11, 12, 13 can be arranged enterable in the control system of the apparatus via a user interface, or the apparatus can be provided with e.g. positioning lights known as such or some other corresponding arrangement via which the desired coordinates can be arranged to be transmitted to the control system automatically. The control system can also include one or more than one preset positions for the imaging means 14, 15 as well as control routines by which more than one kind of volume can be covered. In such case, a control routine can comprise control commands for driving the first 11 and the second arm part 12 to an imaging starting position which is preset or entered in the control system.

The imaging means of the CT apparatus according to the invention includes an area sensor, the so-called frame sensor, used substantially in CBCT imaging. The active surface of the sensor can be circular, rectangular or quadric, the diameter or side length of which being of the order of 10-20 cm. By arranging collimation of the beam produced by the radiation source to correspond the dimensions of such a sensor and by using SID (source-image-distance) of the order of e.g. 50-60 cm, the apparatus according to the invention can image volumes of several sizes in the area of the dental arch.

It is obvious by those skilled in the art that, especially with advancement of technology, the basic idea of the invention can be realized in many different ways, and its different embodiments are not limited to the above examples but they can vary within the scope defined by the accompanied claims. As an example, it can be noted that the term "rotation axis" used in this specification is not intended to be narrowly understood as a physical axis, but it can refer to any virtual axis providing corresponding functionality or a physical pivot, bearing or some other structure.

The invention claimed is:

1. A computed tomography apparatus for odontology, which apparatus comprises an arm part arranged turnable around at least one rotation axis with the help of an actuator, to which arm part and at a distance from each other a radiation source and a receiver of image information have been arranged, said receiver of image information comprising an imaging detector which is an area sensor which during an imaging scan captures a number of frames comprising x-ray image information of the object being imaged, a control system to control said actuator, radiation source and receiver of image information, in which apparatus said arm part is arranged to be located or transferable with respect to the volume desired to become imaged to such location, and the control system to comprise such control routine that when the arm part is turned during an individual imaging scan in which information is gathered for reconstruction of a single volume, at least over a substantial angular range or over the whole angular range used for the individual imaging scan, only a portion of the volume arranged to become imaged is within the radiation beam, characterized in that said control system comprises a first control routine, which is arranged to control said radiation source to produce pulsed radiation and wherein the apparatus comprises a means to measure anode current of the radiation source during an individual radiation pulse and in the event of deviation from a preset value, said first control routine comprises adjusting duration of the radiation pulses such that anode current of the radiation source is measured and the pulse is terminated at the point when integral of the measured current reaches the preset value, whereby upon termination of said radiation pulse the capturing of x-ray image information at said imaging detector also terminates.

2. An apparatus according to claim 1 wherein said control system is arranged to control reading of information from said imaging detector to take place at those moments of time when the irradiation has been interrupted.

3. An apparatus according to claim 1 wherein duration of a single radiation pulse is arranged shorter than the maximum time it may take for the beam to turn in the volume being imaged for a distance which corresponds the voxel size one intends to use in the reconstruction, or shorter or substantially shorter than the time which lapses when said imaging detector moves during imaging a distance of one detector pixel.

4. An apparatus according to claim 1 wherein said imaging detector is a circular, a rectangular or a quadric area sensor, the diameter or the side length of which being of the order of 10-20 cm.

5. An apparatus according to claim 1 wherein said imaging detector has been arranged to save and/or forward the information it has received several times a second.

6. An apparatus according to claim 1 wherein said first control routine comprises controlling the radiation source such that a portion of the pulses is generated with a greater voltage, another portion with a lower voltage.

7. An apparatus according to claim 6, wherein said first control routine comprises generating every other pulse with a higher voltage and every other with a lower voltage, or in consecutive periods during which always the same number of pulses is generated first by the other, then by the other voltage.

8. An apparatus according to claim 1, wherein the apparatus includes
a first arm part arranged turnable about a substantially vertical rotation axis with the help of an actuator to which arm part and at a distance from each other and on the opposite sides of said rotation axis, a radiation source and a receiver of image information have been arranged,
a second arm part arranged turnable about a substantially vertical rotation axis with the help of an actuator which second arm part is arranged to support said first arm part, and in which
said control system comprises a second control routine which controls said at least one actuator of the apparatus such that during an imaging process, said first arm part does not rotate but remains at its place in relation to said second arm part for the duration of imaging, and said second arm part rotates about its rotation axis.

9. An apparatus according to claim 8, wherein said second control routine comprises a step in which, prior to the actual imaging process, the first arm part is driven at a desired angle in relation to the orientation of the second arm part.

10. An apparatus according to claim 8 wherein said second control routine comprises turning the second arm part about its rotation axis substantially for 360 degrees.

11. An apparatus according to claim 8, wherein said first arm part is supported by said second arm part via the rotation axis of the first arm part.

12. An apparatus according to claim 8, wherein the rotation axes of said first and second arm part are substantially parallel and/or the distance between them is constant.

13. An apparatus according to claim 5 wherein said imaging detector has been arranged to save and/or forward the information it has received at least ten times a second.

14. A computed tomography apparatus for odontology, which apparatus comprises an arm part arranged turnable around at least one rotation axis with the help of an actuator, to which arm part and at a distance from each other a radiation source and a receiver of image information have been arranged in a manner to perform an asymmetric scan of at least 360°, a control system to control said actuator, radiation source and receiver of image information, in which apparatus said arm part is arranged to be located or transferable with respect to the volume desired to become imaged to such location, and the control system to comprise such control routine that when the arm part is turned during imaging, at least over a substantial angular range or over the whole angular range used for the imaging, only a portion of the volume arranged to become imaged is within the radiation beam, characterized in that said control system comprises a first control routine, which is arranged to control said radiation source to produce pulsed radiation, and the apparatus comprises a means to measure anode current of the radiation source and that said first control routine comprises adjusting duration of the radiation pulses such that anode current of the radiation source is measured and said pulse is terminated at the point when integral of the measured current reaches a preset value which is associated with an image frame to be generated.

* * * * *